(12) United States Patent
Chludzinski et al.

(10) Patent No.: US 6,837,890 B1
(45) Date of Patent: Jan. 4, 2005

(54) EXPANDED UHMWPE FOR GUIDING CATHETER LINERS AND OTHER LUBRICIOUS COATINGS

(75) Inventors: Matt Chludzinski, Poway, CA (US); Eric Hammill, Lauderdale, MN (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 58 days.

(21) Appl. No.: 10/032,940

(22) Filed: Dec. 26, 2001

(51) Int. Cl.[7] .............................................. A61F 11/00
(52) U.S. Cl. ...................... 606/108; 606/192; 606/194
(58) Field of Search ................................. 606/108, 191, 606/192, 194, 1; 604/96.01, 102.01, 102.02, 264, 104, 103.09, 103.12; 428/36.9

(56) References Cited

U.S. PATENT DOCUMENTS

| | | | |
|---|---|---|---|
| 4,279,245 A | | 7/1981 | Takagi et al. |
| 4,482,516 A | | 11/1984 | Bowman et al. |
| 4,655,769 A | * | 4/1987 | Zachariades ............... 623/1.49 |
| 4,668,557 A | | 5/1987 | Lakes |
| 4,820,466 A | | 4/1989 | Zachariades |
| 4,833,172 A | | 5/1989 | Schwarz et al. |
| 4,876,049 A | * | 10/1989 | Aoyama et al. .............. 264/49 |
| 4,950,151 A | | 8/1990 | Zachariades |
| 5,335,675 A | | 8/1994 | Wheeler, deceased et al. |
| 5,499,973 A | * | 3/1996 | Saab ....................... 604/96.01 |
| 5,569,196 A | | 10/1996 | Muni et al. |
| 5,695,698 A | | 12/1997 | Ajji et al. |
| 5,752,934 A | | 5/1998 | Campbell et al. |
| 5,753,358 A | | 5/1998 | Korleski |
| 5,782,903 A | | 7/1998 | Wiktor |
| 5,783,086 A | | 7/1998 | Scanlon et al. |
| 5,788,626 A | | 8/1998 | Thompson |
| 6,165,166 A | | 12/2000 | Samuelson et al. |
| 6,344,045 B1 | * | 2/2002 | Lim et al. ................... 606/108 |
| 6,428,506 B1 | * | 8/2002 | Simhambhatla et al. . 604/96.01 |
| 6,547,828 B2 | * | 4/2003 | Scott et al. ................... 623/66 |
| 6,602,224 B1 | * | 8/2003 | Simhambhatla .......... 604/96.01 |

FOREIGN PATENT DOCUMENTS

| | | |
|---|---|---|
| EP | 0 253 513 A3 | 1/1988 |
| EP | 0 267 719 A2 | 5/1988 |
| EP | 0 313 263 A3 | 4/1989 |
| EP | 0 376 503 A1 | 7/1990 |

OTHER PUBLICATIONS

D. Breslow et al., "Bis–(cyclopendtadienyl)–titanium Dichloride–Alkylaluminum Complexes as Soluble Catalysts for the Polymerization of Ethylene", J. Am. Chem. Soc., Jan. 5, 1959, p. 81–89, vol. 81.

J. Chien et al., "Ethylene–Hexene Copolymerization by Heterogeneous and Homogeneous Ziegler–Natta Catalysts and the "Comonomer" Effect", J. Polym. Sci. Polym. Chem., 1993, p. 227–237, vol. 31.

U. Zucchini et al., "Behaviour of $[Ti_2(OEt)_8Cl]_2Mg_2(\mu-Cl)_2$ as catalyst component in the Ziegler–Natta polymerization of α–olefins and diolefins", J. Molec. Cat., 1993, p. 45–56, vol. 82.

(List continued on next page.)

*Primary Examiner*—Pedro Philogene
(74) *Attorney, Agent, or Firm*—Fulwider Patton Lee & Utecht, LLP

(57) ABSTRACT

An intraluminal catheter, such as a guiding catheter, employed for intravascular procedures and having an inner liner formed of expanded Ultra High Molecular Weight Polyethylene (UHMWPE) is disclosed. The expanded UHMWPE is microporous and has an oriented microstructure structure characterized by nodes interconnected by fibrils. The inner liner formed of expanded UHMWPE is very thin to maximize the inner lumen diameter and has excellent mechanical properties.

21 Claims, 2 Drawing Sheets

OTHER PUBLICATIONS

U.S. Appl. No. 09/713,642, filed Nov. 14, 2000, "Medical Device Formed of Ultrahigh Molecular Weight Polyolefin".

Caddock et al. "Microporous materials with negative Poisson's ratios: I. Microstructure and mechanical properties", Journal of Physics D: Applied Physics, 22(12): p. 1877–1882 (1989).

Evans et al. "Microporous materials with negative Poisson's ratios: II. Mechanisms and interpretation", Journal of Physics D: Applied Physics 22 p. 1883–1887 (1989).

Pickles et al "The effect of the processing parameters on the fabrication of auxetic polyethlene" Part I The effect of compaction conditions, Journal of Material Science 30 p. 4059–4068 (1995).

Alderson et al "The effect of the processing parameters on the fabrication of auxetic polyethlene" Part II The effect of sintering temperature and time, Journal of Material Science 30 p. 4069–4075 (1995).

Neale et al "The effect of the processing parameters on the fabrication of auxetic polyethlene" Part III The effect of extrusion conditions, Journal of Material Science 30 p. 4087–4094 (1995).

Evans et al "The static and dynamic moduli of auxetic microporous polyethlene", Journal of Material Science Letters 11 p. 1721–1724 (1992).

Alderson et al "Strain–dependent behaviour of microporous polyethylene with a negative Poisson's ratio", Journal of Material Science 28 p. 4092–4098 (1993).

Alderson et al. "Auxetic Polyethlene: the Effect of a Negative Poisson's Ratio on Hardness" Acta metall. Mater. vol. 42, No. 7 pp. 2261–2266 (1994).

Alderson et al "The interpretation of the strain–dependent Poisson's ratio in auxetic polyethylene", Journal of Strain Analysis vol. 32 No. 3 p. 201–212 (1997).

Alderson et al "Modelling concurrent deformation mechanisms in auxetic microporous polymers" Journal of Material Science 32 p. 2797–2809 (1997).

Pickles et al "The Effects of Powder Morphology on the Processing of Auxetic Polypropylene (PP of Negative Poisson's Ratio)" Polymer Engineering and Science, Mid–Mar. vol. 36, No. 5 p. 636–642 (1996).

Alderson et al "Microstructural modelling of auxetic microporous Polymers" Journal of Material Science 30 p. 3319–3332 (1995).

Internet Web Site –http//www.devicelink.com/mpb/archive/98/03/003.html, Bajaria et al "Deformation, Morphology, and Wear Behavior of Polyethylene Used in Orthopedic Implants", (Medical Platics and Biomaterials Magazine MPB Article Index, 11 Pgs., visited Oct. 17, 2001—Originally published Mar. 1998.

* cited by examiner

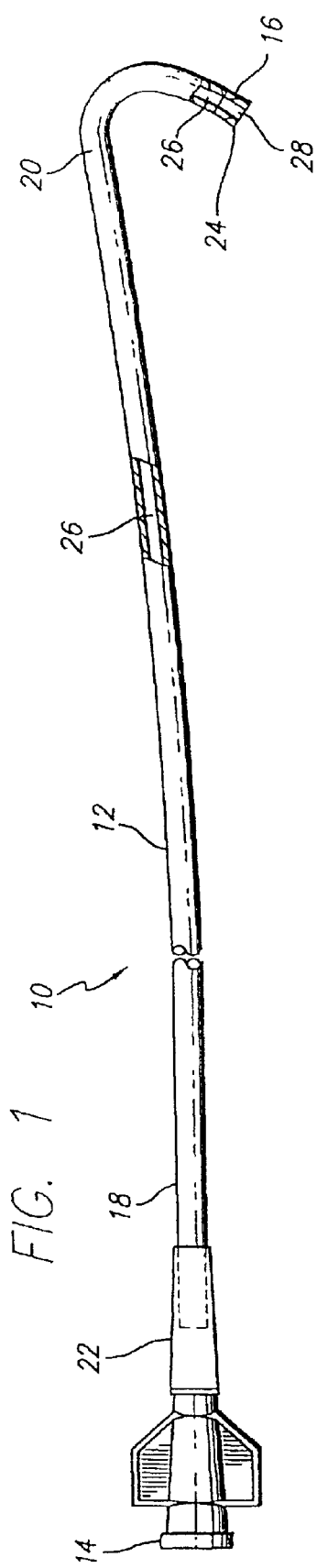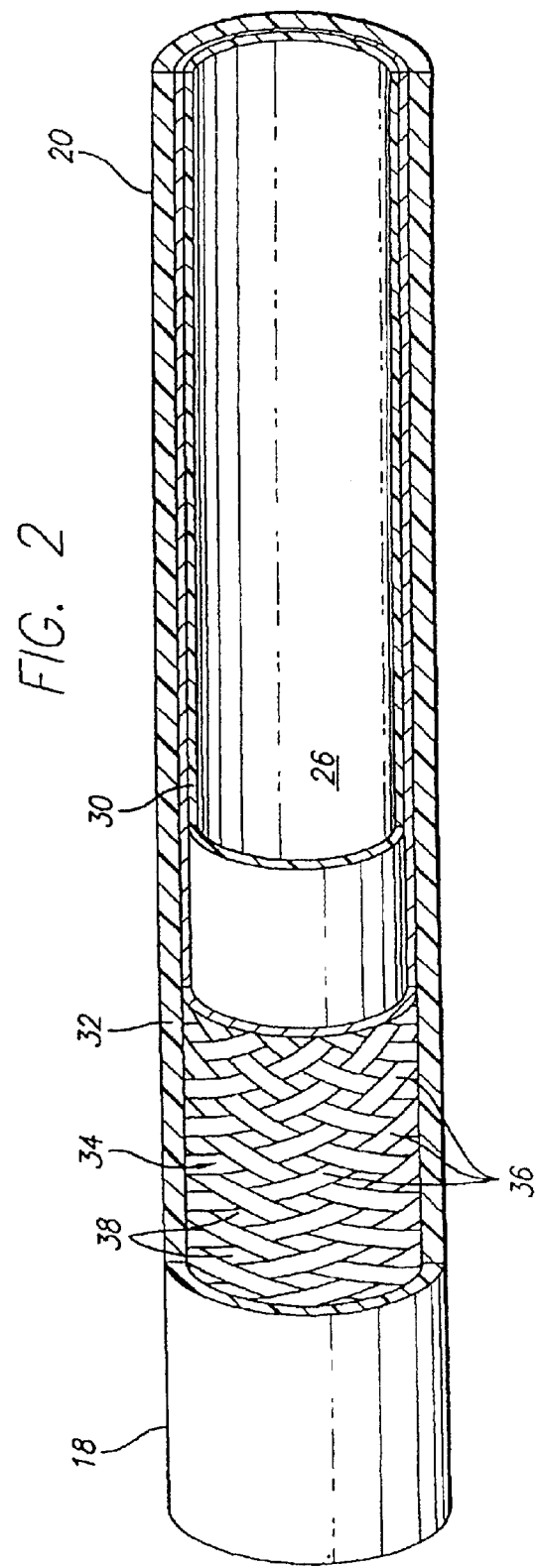

EXPANDED UHMWPE FOR GUIDING CATHETER LINERS AND OTHER LUBRICIOUS COATINGS

BACKGROUND OF THE INVENTION

The invention relates to the field of intraluminal catheters, and particularly to guiding catheters suitable for intravascular procedures such as angioplasty, stent deployment, pacing lead deployment and the like.

In percutaneous transluminal coronary angioplasty (PTCA) procedures, a guiding catheter having a shaped distal section is percutaneously introduced into a patient's vasculature and then advanced through the patient's vasculature until the shaped distal section of the guiding catheter is adjacent to the ostium of a desired coronary artery. The proximal end of the guiding catheter, which extends out of the patient, is torqued to rotate the shaped distal section and, as the distal section rotates, it is guided into the desired coronary ostium. The distal section of the guiding catheter is shaped so as to engage a surface of the ascending aorta and thereby seat the distal end of the guiding catheter in the desired coronary ostium and to hold the catheter in that position during the procedures when other intravascular devices such guide wires and balloon catheters are being advanced through the inner lumen of the guiding catheter.

In the typical PTCA or stent delivery procedures, the balloon catheter with a guide wire disposed within an inner lumen of the balloon catheter is advanced within the inner lumen of the guiding catheter which has been appropriately positioned with its distal tip seated within the desired coronary ostium. The guide wire is first advanced out of the distal end of the guiding catheter into the patient's coronary artery until the distal end of the guide wire crosses a lesion to be dilated or an arterial location where a stent is to be deployed. A balloon catheter is advanced into the patient's coronary anatomy over the previously introduced guide wire until the balloon on the distal portion of the balloon catheter is properly positioned across the lesion. Once properly positioned, the balloon is inflated with inflation fluid one or more times to a predetermined size so that, in the case of the PTCA procedure, the stenosis is compressed against the arterial wall and the wall expanded to open up the vascular passageway. In the case of stent deployment, the balloon is inflated to plastically expand the stent within the stenotic region where it remains in the expanded condition. Generally, the inflated diameter of the balloon is approximately the same diameter as the native diameter of the body lumen being dilated so as to complete the dilatation or stent deployment but not overexpand the artery wall. After the balloon is finally deflated, blood flow resumes through the dilated artery and the dilatation catheter and the guide wire can be removed therefrom. Generally, the stent deployment may be accomplished simultaneously with or after a PTCA procedure has been performed at the stenotic site.

In addition to their use in PTCA and stent delivery procedures, guiding catheters are used to advance a variety of electrophysiology-type catheters and other therapeutic and diagnostic devices into the coronary arteries, the coronary sinus, the heart chambers, neurological and other intracorporeal locations for sensing, pacing, ablation, and other procedures. For example, one particularly attractive procedure for treating patients with congestive heart failure (CHF) involves introduction of a pacing lead into the patient's coronary sinus and advancing the lead through the patient's great coronary vein and a branch of the great coronary vein until the distal end of the pacing lead is disposed at a location which allows the electrical impulses from the pacing lead to pace the left ventricle of the patient's heart. A second pacing lead may be disposed within the patient's right ventricle or a cardiac vein draining the patient's right ventricle and both the left and right ventricle may then be paced by the pacing leads, resulting in greater pumping efficiencies and greater blood flow out of the heart which minimizes the effects of CHF.

Commercially available guiding catheters are typically constructed of a lubricious, polymeric inner liner, a polymeric outer jacket, and a reinforcing structure disposed between the inner liner and outer jacket formed of woven, braided, or wound strands which are usually metallic, high strength polymers or combinations thereof. The lubricious inner liner serves to diminish the frictional forces generated from the passage of interventional devices within the inner lumen. The lubricious inner liner is commonly formed of polytetrafluoroethylene (PTFE) because of its low coefficient of friction.

The conventional PTFE inner liner is relatively thin. Further reduction in its wall thickness is difficult, because the PTFE liner would lack the physical integrity to withstand the caustic chemical etching typically used to bond it to other catheter components.

On the other hand, clinical requirements for utilizing guiding catheters to advance catheters and other intravascular devices have resulted in a need for increased transverse dimensions of the inner lumens of guiding catheters to accommodate a greater variety of large intracorporeal devices with little or no increase in the outer transverse dimensions of the guiding catheter to present a low profile which facilitates advancement within the patient's body lumens and openings. These catheter design changes have required a reduction in total wall thickness, including a reduction in the thickness of the inner liner. It would thus be desirable to provide a thinner inner liner to maximize the inner lumen diameter. Alternatively, a reduction in the thickness of the inner liner would permit a reduction in the outer transverse dimensions of the catheter to ease passage through narrow, tortuous blood vessels or an increase in the thickness of the other catheter layers for greater strength without increasing the outer profile. A suitable thinner inner liner should still provide the requisite physical and mechanical properties for its use, such as lubricity, flexibility, and sufficient strength and integrity. In addition, it would be desirable if the inner liner material had physical characteristics which would not be compromised by radiation sterilization.

What has been needed is a catheter design incorporating a thinner inner liner with clinically-desirable characteristics. The present invention satisfies these and other needs.

SUMMARY OF THE INVENTION

The invention is generally directed to an intraluminal catheter, such as a guiding catheter, with a an inner liner including expanded Ultra High Molecular Weight Polyethylene (UHMWPE).

One embodiment of the present invention intraluminal catheter comprises an elongated shaft which includes expanded UHMWPE and has a proximal end, a distal end, and an inner lumen extending longitudinally therethrough. The expanded UHMWPE is microporous and has a node and fibril microstructure comprising nodes interconnected by fibrils. The expanded UHMWPE may be included in an inner liner defining the inner lumen of the elongated shaft.

The expanded UHMWPE may also be included in an exterior lubricious coating on the elongated shaft.

In one embodiment, the inner liner including expanded UHMWPE has a thickness of about 0.0002 to about 0.0006 inch. In other embodiments, it has a thickness of less than about 0.0005 inch, and a thickness of about 0.00025 inch. In yet another embodiment, the inner liner including expanded UHMWPE has a porosity of about 20 to about 90 percent.

The elongated shaft may further include a polymeric outer jacket extending over the inner liner and a reinforcing structure disposed between the polymeric outer jacket and the inner liner. In one embodiment, the combined thickness of the inner liner, reinforcing structure and polymeric outer jacket is about 0.004 to about 0.005 inch. Optionally, the inner liner is impregnated with a polymer which is compatible with the polymeric outer jacket and is fusion bonded to the polymeric outer jacket. The impregnated polymer and polymeric outer jacket may be formed of PEBAX and fusion bonded together. Also, the inner liner may be secured to the polymeric outer jacket with a tie layer of a compatibilizing material.

In another embodiment, the invention comprises a guiding catheter having an elongated shaft having a proximal end, a distal end, an inner lumen extending longitudinally therethrough, and an inner liner defining the inner lumen which includes expanded UHMWPE and has a thickness of about 0.0002 to about 0.0006 inch.

In various embodiments, the present invention further provides methods for manufacturing an intraluminal catheter with an inner liner including expanded UHMWPE comprising bonding a tubular inner liner including expanded UHMWPE to a polymeric outer jacket extending over the inner liner. The inner liner is bonded to the polymeric outer jacket by impregnating the inner liner with a polymer which is compatible with the polymeric outer jacket and heat fusing the impregnated polymer in the inner liner to the polymeric outer jacket.

The present invention provides intraluminal catheters with improved characteristics due to the use of expanded UHMWPE as an inner liner. The inner liner formed of eUHMPWE is thinner than those currently employed because it is a stronger material which has sufficient integrity to be suitably bonded to other catheter components despite its thinness. This inner liner maximizes the diameter of the inner lumen relative to the outer profile of the catheter. The expanded UHMWPE inner liner also contains other desirable properties such as high lubricity, high flexibility, and resistance to flaking during abrasion. Further, expanded UHMWPE is radiation stable, unlike PTFE, permitting catheter sterilization by radiation, such as gamma rays or electron beams. Radiation sterilization improves the manufacturability of catheters as it can be quickly performed in the manufacturing line, while the ethylene oxide gas sterilization procedure, typically used with PTFE-lined catheters, requires storage for up to 48 hours to allow the gas to diffuse out of the sterilized equipment.

Furthermore, expanded UHMWPE has low processing temperatures, so it can be easily bonded to a variety of other polymeric catheter components. In contrast, PTFE has high processing temperatures not as suitable for many common polymeric materials used in catheters.

These and other advantages of the invention will become more apparent from the following detailed description of the invention and the accompanying exemplary drawings.

BRIEF DESCRIPTION OF THE DRAWINGS

FIG. 1 is a side elevational view of a guiding catheter embodying features of the present invention.

FIG. 2 is a partial cutaway perspective view of the elongated shaft of the catheter shown in FIG. 1.

DETAILED DESCRIPTION OF THE PREFERRED EMBODIMENTS

Figure 3:
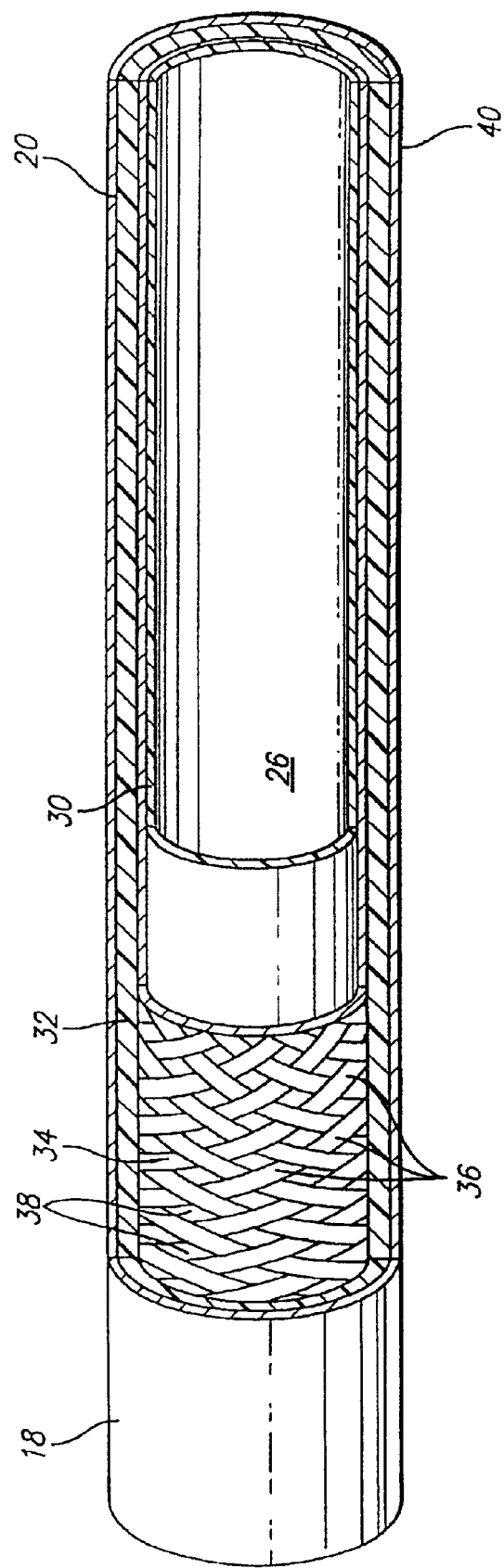
FIG. 3 is a partial cutaway perspective view of another embodiment of the present invention in which the elongated shaft has an exterior lubricious coating.

FIG. 1 illustrates an embodiment of the present invention catheter 10 generally including an elongated catheter shaft 12 with a proximal end 14 and a distal end 16. The elongated catheter shaft 12 also has a proximal shaft section 18 and a distal shaft section 20 which is at least partially shaped, an adapter 22 mounted on the proximal end 14, a non-traumatic distal tip 24, and an inner lumen 26 which extends within the catheter shaft 12 from the proximal end 14 thereof to a port 28 located in the distal end 16 of the shaft. The adapter 22 on the proximal end 14 of the catheter 10 may be formed of conventional polymeric materials such as polycarbonate.

As shown in greater detail in FIGS. 2 and 3, elongated catheter shaft 12 has an inner liner 30 and a polymeric outer jacket 32. A reinforcing structure 34 formed of multiple, interweaved strands 36 is disposed between inner liner 30 and polymeric outer jacket 32. Spaces 38 are formed in the reinforcing structure 34 allowing contact between the polymeric outer jacket 32 and the inner liner 30. FIG. 3 additionally shows an optional, exterior lubricious coating 40 formed around the polymeric outer jacket 32 of elongated catheter shaft 12.

The inner liner 30 is a tubular member formed of expanded Ultra High Molecular Weight Polyethylene (i.e., expanded UHMWPE or eUHMWPE). The expanded UHMWPE inner tubular member may extend through the entire length of the shaft, although the non-traumatic distal tip 24 may be formed with a different polymeric material.

With regard to the material, the expanded UHMWPE in one embodiment is formed of basic UHMWPE, a polyethylene with a molecular weight typically between about 2 million and about 10 million grams/mole, that has been expanded or drawn to deform the UHMWPE into a microporous material exhibiting an oriented microstructure of nodes interconnected by fibrils. In this embodiment, the expanded UHMWPE may have a porosity of about 20% to about 90%. Examples of expanded, microporous UHMWPE having a node and fibril microstructure, and a suitably high orientation with an anisotropic structure or at least significant anisotropy in the structure arc described in PCT International Publication No. WO 91/01210 (Evans), incorporated by reference herein in its entirety. As described in WO 91/01210, such UHMWPE materials may exhibit a negative Poisson ratio.

The reinforcing structure 34 and polymeric outer jacket 32 may have a conventional construction. That is, the strands 36 that are woven, braided, or wound to form the reinforcing structure 34 may be formed of metal, high strength polymers, or a combination thereof. Suitable materials include stainless steel, nickel-titanium alloys, i.e., nitinol, aramid (Kevlar), nylon, or polyester (Dacron). The reinforcing structure 34 may be formed of a continuous structure throughout the elongated catheter shaft 12. In addition, the reinforcing structure 34 may extend through most of the length of the elongated catheter shaft except for the distal tip which is usually provided with a relatively flexible non-reinforced polymeric tubular member to provide non-traumatic characteristics to the distal tip.

The polymeric outer jacket 32 may be composed of various materials and compositions of varying stiffness. The polymeric outer jacket 32 of the proximal section 18 is preferably formed of a stiffer material than that of the distal section 20. Furthermore, the polymeric outer jacket 32 may be formed of a series of polymeric materials having distally decreasing stiffness. Employing variable stiffness along the length of the elongated shaft 12 provides the necessary stiffness for pushability as well as sufficient distal flexibility to permit maneuvering inside the patient's vasculature. The polymeric outer jacket 32 may be formed of a variety of thermoplastic and thermoelastic polymers, copolymers and blends. Suitable materials include polyamide, polyurethane, polyvinyl chloride, and polyethylene. In particular, the polymeric outer jacket 32 may be a polyamide elastomer, e.g., a polyether block amide such as PEBAX of various durometers alone or blended with nylon.

A process of forming the microporous node and fibril structure of the expanded UHMWPE generally entails compacting UHMWPE powder into a billet and then deforming the billet through a die and orienting the extrudate to impart the node and fibril structure. The step of compacting the polyethylene powder can be performed by any suitable means including applying pressure, with or without additional heat, or forming a slurry with a lubricating medium and then compacting the slurry into a billet. The lubricating medium is typically evaporated from the slurry after the extrusion of the billet through a die as is discussed below to impart the oriented node and fibril structure. For extrusion without a mineral oil lubricating medium, the polymer billet may optionally be sintered at temperatures exceeding the crystalline melting point of the polymer. After being compacted, the UHMWPE is then deformed to impart the oriented node and fibril structure. Typically, the UHMWPE is deformed by extrusion through a die followed by uniaxial or biaxial stretching of the extrudate. The deformation step may be performed either at ambient or elevated temperatures.

In one embodiment, sintered polyethylene is ram extruded at ambient temperature to form a sheet of material, which is then stretched, uniaxially or biaxially, to orient the structure. Optionally, the stretched material can be heat set. The processing of the UHMWPE also renders it microporous, and the amount of stretch experienced by the material controls the distance between the nodes and the corresponding fibril length.

The size and shape of the UHMWPE particles of the UHMWPE powder can be chosen to influence the node and fibril structure and optimize the properties of the resulting material. For example, the particle morphology determines the coarseness of the node and fibril structure and the ease of fibrillation during the deformation of the billet through a die. In one embodiment, the UHMWPE particles used to prepare the compacted polyethylene comprise an aggregate of primary particles. The aggregate has a diameter of about 100 $\mu$m to about 700 $\mu$m, and more particularly about 200 $\mu$m to about 400 $\mu$m, in size and is composed of aggregated or fused primary UHMWPE particles having a size of about 0.1 $\mu$m to about 40 $\mu$m, and preferably about 0.1 $\mu$m to about 20 $\mu$m. A suitable aggregate UHMWPE is grade GUR 2122, available from Ticona. Nonaggregated UHMWPE particles having a particle size of less than about 10 $\mu$m may be used to make the node and fibril structure materials, provided handling and safety problems associated with such fine particles are avoided.

The synthesis of UHMWPE is known to occur by Ziegler-Natta catalysis using a transition metal catalyst such as titanium, chromium or zirconium, and a cocatalyst such as aluminum. The nature of the catalyst and the order of the addition of the catalyst and co-catalyst affect the morphology of the resulting polymer. To synthesize material comprising an aggregate of a primary particle as discussed above, preferably a suspension polymerization of ethylene is used with a catalyst such as biscyclopentadienyl titanium dichloride, biscyclopentadienylzircomium dichloride, or cyclopentadienyl zirconium trichloride, and a co-catalyst such as trialkylaluminum, soluble in an alkane medium such as heptane or hexane. The trialklyaluminum co-catalysts include triethyl aluminum, tri-isopropylaluminum, and tributylaluminum. The synthesis of UHMWPE by Ziegler-Natta Catalysis is described in D. Breslow et al., J. Am. Chem. Soc., 31, 81–86 (1959), J. Chien et al., J. Polym. Sci. Polym. Chem., 31, 227–237 (1993), and U. Zucchini et al., J. Molec. Cat., 82, 45–56 (1993), incorporated in their entireties by reference herein. An open aggregate structure can be formed by the control of the polymerization rate, with use of a particular temperature and catalyst, which affects the particle stability and dynamics of aggregation.

As mentioned above, one method of, forming the UHMWPE generally comprises preparing a homogeneous paste of UHMWPE in a low boiling mineral oil. The paste is then compacted into a billet by applying pressure and optionally applying heat. The billet is then loaded into a ram extruder and a tube or film is extruded. The extrusion may be done at room temperature, or the temperature may be elevated. The oil is then evaporated from the UHMWPE by heating the film to a temperature not exceeding the crystalline melting point of the UHMWPE. The film or tube is then uniaxially or biaxially oriented to produce the oriented node and fibril structure. The oriented tube may then optionally be heat set at temperatures just above the melting point of UHMWPE, which has a crystalline melting point of about 130–140° C.

Another process comprises compacting UHMWPE particles into a billet at temperatures below the crystalline melting point of the polymer. Preferably, this step would be done at about 100° C. to about 120° C. The pressure applied is about 0.01 GPa to about 0.08 GPa, and in one embodiment about 0.01 GPa to about 0.1 GPa. The billet is then sintered at temperatures above the crystalline melting point of the polymer without applying any pressure. This step is completed at a temperature of about 130° C. to about 160° C. The sintered billet is extruded through a film or annular die in a ram extruder. The UHMWPE is then optionally oriented and heat set as described above.

The expanded UHMWPE material may be directly produced as a tubular member. Alternatively, the inner liner 30 can be formed from a film of the expanded UHMWPE. The expanded UHMWPE film is wrapped around a mandrel to form a tube and then heated to fuse the wrapped material together. The inner liner 30 can also be formed from a tape of the expanded UHMWPE which is wound around a mandrel and then heat fused to form a tube.

The resulting tubular member may be joined to the other catheter components. Typically, the woven, braided, or wound reinforcing structure 34 is formed around the outside of the tubular inner liner 30. The polymeric outer jacket 32 may then be provided on the exterior of the reinforcing structure 34 by suitable means, preferably by heat shrinking a polymeric layer of the desired composition onto the surface of the reinforcing structure 34. When applied, the outer jacket material flows through the spaces 38 in the woven, braided, or wound reinforcing structure 34 to bond to the inner liner 30. A removable mandrel may be used within the inner lumen 26 defined by the inner liner 30 during the manufacturing process to support and shape the catheter into its desired configuration while it is being formed.

The expanded UHMWPE inner liner 30 and polymeric outer jacket 32 may be secured together by any suitable method. In one embodiment, the inner liner 30 is impregnated with a polymer that is compatible with the outer jacket material. The polymer may be impregnated into the inner liner 30 by dissolving the polymer in a suitable solvent and applying the resulting solution to the inner liner 30 to allow it to impregnate the pores of the material. Optionally, the polymeric outer jacket 32 and the impregnating polymer are both formed of PEBAX. One common solvent for preparing a PEBAX solution is tetrahydrafuran (THF). The solution may be applied to the inner liner 30 by any of a number of ways, such as by injecting the resulting solution into the inner liner 30 by syringe or by brushing the solution on the outer surface of the inner liner 30. The solvent is then removed by evaporation at room temperature or by application of heat in an oven. The polymer in the solution remains mechanically locked within the porous structure of the inner liner 30. When the polymeric outer jacket 32 is applied be heat shrinking, it fuses to the compatible impregnated polymer in inner liner 30, thus securing the inner liner 30 and polymeric outer jacket 32 together.

In another embodiment, a tie layer of a compatiblizing material, such as PRIMACOR, is used to attach the expanded UHMWPE inner liner 30 with an incompatible material forming the polymeric outer jacket 32. The compatibilizing material may be applied to the outer surface of the inner liner 30 using conventional techniques. When the polymeric outer jacket 32 is applied to the catheter by heat shrinking, the compatibilizing material forms a fusion bond with the inner liner 30 and the polymeric outer jacket 34 to secure them together.

Optionally, expanded UHMWPE may be applied as a very thin, exterior lubricious coating 40 on guiding catheters or other intraluminal catheters, including electrophysiology catheters, angiography catheters, and angioplasty catheters, to ease passage through the patient's vasculature.

Guiding catheters designed for coronary artery access have varying lengths, generally between about 90 to about 130 cm, and more commonly the length is about 100 to about 120 cm. Catheters embodying features of the invention for providing access to the coronary arteries or cardiac veins through the coronary sinus have an inner diameter of about 0.06 to about 0.09 inch, and a wall thickness of about 0.004 to about 0.006 inch. In one exemplary embodiment, the wall thickness of the elongated catheter shaft 12 is about 0.004 to about 0.005 inch. The thickness of the inner liner 30 is about 0.0002 to about 0.006 inch. The thickness of inner liner 30 is less than 0.0005 inch, and in another embodiment, it is about 0.00025 inch. The guiding catheter has a generally constant inner and outer diameter throughout its length, and the wall thickness is also generally constant.

The present invention contemplates using expanded UHMWPE in conjunction with fillers, additives, or other polymers to produce inner liners or exterior coatings formed partially of expanded UHMWPE. The specific construction and chemical compositions of such fillers, additives, coatings, liners, and the like are known in the art.

It will be apparent from the foregoing that, while particular forms of the invention have been illustrated and described, various modifications can be made without departing from the spirit and scope of the invention. Moreover, those skilled in the art will recognize that features shown in one embodiment of the invention may be utilized in other embodiments of the invention. To the extent not otherwise described herein, the materials and methods of construction and the dimensions of conventional intravascular guide wires may be employed with the guiding member embodying features of the present invention. While the description of the invention is directed to embodiments for coronary applications, various modifications and improvements can be made to the invention without departing therefrom. Additionally, reference to the terms "members," "elements," "sections" and terms of similar import in the claims which follow shall not be interpreted to invoke the provisions of 35 U.S.C. §112 (paragraph 6) unless reference is expressly made to the term "means" followed by an intended function.

What is claimed is:

1. An intraluminal catheter, comprising:
an elongated shaft having a proximal end, a distal end, a proximal shaft section, a distal shaft section which is more flexible than the proximal shaft section, and an inner lumen extending longitudinally therethrough, the shaft having at least a layer comprising expanded UHMWPE, wherein the expanded UHMWPE is microporous and has a node and fibril microstructure comprising nodes interconnected by fibrils.

2. The intraluminal catheter of claim 1, wherein the shaft includes an inner liner defining the inner lumen, the inner liner including the expanded UHMWPE.

3. The intraluminal catheter of claim 2, wherein the inner liner has a thickness of about 0.0002 to about 0.0006 inch.

4. The intraluminal catheter of claim 2, wherein the inner liner has a thickness of less than about 0.0005 inch.

5. The intraluminal catheter of claim 2, wherein the inner liner has a thickness of about 0.00025 inch.

6. The intraluminal catheter of claim 2, wherein the inner liner has a porosity of about 20 to 90 percent.

7. The intraluminal catheter of claim 2, wherein the shaft further includes a polymeric outer jacket extending over the inner liner and a reinforcing structure disposed between the polymeric outer jacket and the inner liner.

8. The intraluminal catheter of claim 7, wherein the polymeric outer jacket, reinforcing structure and inner liner have a combined thickness of about 0.004 to about 0.005 inch.

9. The intraluminal catheter of claim 7, wherein the inner liner is impregnated with a polymer which is compatible with the polymeric outer jacket.

10. The intraluminal catheter of claim 9, wherein the impregnated polymer in the inner liner is fusion bonded to the polymeric outer jacket.

11. The intraluminal catheter of claim 9, wherein the impregnated polymer in the inner liner and the polymeric outer jacket are formed of PEBAX.

12. The intraluminal catheter of claim 11, wherein the impregnated polymer in the inner liner is fusion bonded to the polymeric outer jacket.

13. The intraluminal catheter of claim 8, wherein the inner liner is secured to the polymeric outer jacket with a tie layer of a compatibilizing material.

14. The intraluminal catheter of claim 1, wherein the shaft includes a lubricious exterior coating including the expanded UHMWPE.

15. A catheter, comprising:
an elongated shaft having a proximal end, a distal end, an inner lumen extending longitudinally therethrough to a port in the distal end of the catheter shaft, a length of about 90 to about 130 cm, and an inner liner defining the inner lumen, the inner liner comprising microporous expanded UHMWPE and having a thickness of about 0.00025 to about 0.0005 inch.

16. A method for manufacturing an intraluminal guiding catheter shaft with an inner liner including expanded UHMWPE, comprising:

providing a polymeric outer jacket;

providing a tubular inner liner including expanded UHMWPE;

providing a reinforcing structure;

disposing the tubular inner liner within the polymer outer jacket with the reinforcing structure therebetween; and bonding the tubular inner liner to the polymeric outer jacket and fusing the reinforcing structure therebetween.

17. The method of claim 16, wherein bonding the inner liner to the polymeric outer jacket further comprises:

impregnating the inner liner with a polymer which is compatible with the polymeric outer jacket; and heat fusing the impregnated polymer in the inner liner to the polymeric outer jacket.

18. The method of claim 16, wherein bonding the inner liner to the polymeric outer jacket further comprises:

applying a compatibilizing material between the inner liner and polymeric outer jacket to act as a tie layer; and heat fusing the compatibilizing material to the inner liner and the polymeric outer jacket.

19. An intraluminal guiding catheter, comprising:

an elongated shaft having a proximal end, a distal end, an inner lumen extending longitudinally therethrough, a polymeric outer layer, and an inner liner comprising expanded UHMWPE, wherein the shaft includes varying stiffness along its length; and an open-walled reinforcing structure disposed coaxially over the inner liner between the inner liner and the polymeric outer layer, the reinforcing structure, inner liner, and polymeric outer layer being fixedly secured together.

20. The intraluminal catheter of claim 19, wherein the reinforcing structure includes at least one of a weave, braid, and winding of a material selected from the group consisting of stainless steel, nickel-titanium, aramid, nylon, or polyester.

21. An intraluminal guiding catheter, comprising:

an elongated shaft having a proximal end, a distal end, and an inner lumen extending longitudinally therethrough, the shaft including expanded UHMWPE, wherein the expanded UHMWPE is microporous and has a node and fibril microstructure comprising nodes interconnected by fibrils; and where in the shaft further includes a polymeric outer jacket and a non-implantable reinforcing structure fused into the shaft.

* * * * *